(12) United States Patent
Eddaoudi et al.

(10) Patent No.: US 10,377,786 B2
(45) Date of Patent: Aug. 13, 2019

(54) GREEN METHODS FOR PREPARING HIGHLY CO2 SELECTIVE AND H2S TOLERANT METAL ORGANIC FRAMEWORKS

(71) Applicant: King Abdullah University of Science and Technology, Thuwal (SA)

(72) Inventors: Mohamed Eddaoudi, Thuwal (SA); Osama Shekhah, Thuwal (SA); Youssef Belmabkhout, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 38 days.

(21) Appl. No.: 15/319,505

(22) PCT Filed: Jun. 17, 2015

(86) PCT No.: PCT/US2015/036212
§ 371 (c)(1),
(2) Date: Dec. 16, 2016

(87) PCT Pub. No.: WO2015/195791
PCT Pub. Date: Dec. 23, 2015

(65) Prior Publication Data
US 2017/0137450 A1     May 18, 2017

Related U.S. Application Data

(60) Provisional application No. 62/012,982, filed on Jun. 17, 2014.

(51) Int. Cl.
| | | |
|---|---|---|
| C07F 15/04 | (2006.01) | |
| B01J 20/22 | (2006.01) | |
| B01J 20/30 | (2006.01) | |
| B01J 37/00 | (2006.01) | |
| C07F 7/02 | (2006.01) | |
| B01J 31/16 | (2006.01) | |
| B01J 37/04 | (2006.01) | |

(52) U.S. Cl.
CPC ........... *C07F 15/045* (2013.01); *B01J 20/226* (2013.01); *B01J 20/3078* (2013.01); *B01J 20/3085* (2013.01); *B01J 31/1691* (2013.01); *B01J 37/009* (2013.01); *B01J 37/04* (2013.01); *C07F 7/025* (2013.01); *B01J 2231/005* (2013.01); *B01J 2531/16* (2013.01); *B01J 2531/26* (2013.01); *B01J 2531/847* (2013.01)

(58) Field of Classification Search
None
See application file for complete search history.

(56) References Cited

FOREIGN PATENT DOCUMENTS

WO          2013112792 A1      8/2013

OTHER PUBLICATIONS

"International Search Report and Written Opinion", International Application No. PCT/US2015/036212, Sep. 17, 2015, 13 pages.
Adams, "Supporting Information-Solod State Interconversions of Coordination Networks and Hydrogen-Bonded Salts", Retrieved from Internet: URL:http://www.wiley-vch.de/contents/jc_2002/2007/z603593_s.pdf [retrieved on Sep. 11, 2015], Jan. 1, 2007, 1-24.
Al-Maythalony, et al., "Quest for Anionic MOF Membranes: Continuous sod-ZMOF Membrane with CO2 Adsorption-Driven Selectivity", J. Am. Chem. Soc. 2015, 137, 1754-1757.
Baker, "Membrane Technology and Applications", Wiley, 2012.
Bayliss, et al., "Synthesis of metal-organic frameworks by continuous flow", Green Chemistry, vol. 16, No. 8, Jan. 1, 2014, 3796.
Betard, et al., "Metal-Organic Framework Thin Films: From Fundamentals to Applications.", Chemical Reviews, 2012, 112, 1055-1083.
Bohrman, et al., "Synthesis and CO2/CH4 separation performance of Bio-MOF-1 membranes", Chem. Commun., 2012, 48, 5130-5132.
Bowmaker, et al., "Solvent-assisted mechanochemical synthesis of metal complexes", Dalton Transactions, No. 22, Jan. 1, 2008, 2926.
Brunetti, et al., "Membrane technologies for CO2 separation", Journal of Membrane Science 359 (2010) 115-125.
Ding, et al., "Hydrothermal syntheses and characterization of a series of luminescent Cd(ii) frameworks with pyridine-based and benzene-based bis-triazole ligands", Crystengcomm, vol. 15, No. 13, Jan. 1, 2013, 2490.
Friscic, et al., "Clean and Efficient Synthesis Using Mechanochemistry: Coordination Polymers, Metal-Organic Frameworks and Metallodrugs", Croat. Chem. Acta 85 (3) (2012) 367-378.
Friscic, et al., "Mechanochemical conversion of a metal oxide into coordination polymers and porous frameworks using liquid assisted grinding(LAG)", Crystengcomm, vol. 11, No. 5, Jan. 1, 2009, 743.
Ibarra, et al., "Near-critical water, a cleaner solvent for the synthesis of a metal—organic framework", Green Chem., 2012,14, 117-122.

(Continued)

*Primary Examiner* — Samantha L Shterengarts
(74) *Attorney, Agent, or Firm* — Billion & Armitage; Benjamin C. Armitage

(57) ABSTRACT

A green route for preparing a metal organic framework include mixing metal precursor with a ligand precursor to form a solvent-free mixture; adding droplets of water to the mixture; heating the mixture at a first temperature after adding the water; and isolating the metal organic framework material including the metal and the ligand.

20 Claims, 6 Drawing Sheets

(56) References Cited

OTHER PUBLICATIONS

Kuppler, et al., "Potential applications of metal-organic frameworks", Coordination Chemistry Reviews, 2009, 253, 3042-3066.

Li, et al., "Metal-Organic Frameworks for Separations", Chem. Rev., 2012, 112, 869-932.

Liu, et al., "Enantiopure Metal—Organic Framework Thin Films: Oriented SURMOF Growth and Enantioselective Adsorption", Angew. Chem. Int. Ed. 2012, 51, 807-810.

Marquez, et al., "Green Microwave Synthesis of MIL-100(Al, Cr, Fe) Nanoparticles for Thin-Film Elaboration", Eur. J. Inorg. Chem., 2012: 5165-5174.

Marquez, et al., "Green scalable aerosol synthesis of porous metal—organic frameworks", Chem. Commun., 2013,49, 3848-3850.

Mottillo, et al., "Mineral neogenesis as an inspiration for mild, solvent-free synthesis of bulk microporous metal—organic frameworks from metal (Zn, Co) oxides", Green Chem., 2013,15, 2121-2131.

Nugent, et al., "Porous materials with optimal adsorption thermodynamics and kinetics for CO2 separation", Nature, 2013, 495, 80-84.

Rutherford, et al., "Review of Time Lag Permeation Technique as a Method for Characterisation of Porous Media and Membranes", Adsorption 3, 283-312 (1997).

Shah, et al., "Current Status of Metal—Organic Framework Membranes for Gas Separations: Promises and Challenges", Ind. & Eng. Chem. Res. 2012, 51, 2179-2199.

Shekhah, et al., "A facile solvent-free synthesis route for the assembly of a highly CO2 selective and H2S tolerant NiSIFSIX metal—organic framework", Chem. Commun., 2015, 51, 13595--13598.

Shekhah, "Layer-by-Layer Method for the Synthesis and Growth of Surface Mounted Metal—Organic Frameworks (SURMOFs)", Materials 2010, 3, 1302-1315.

Shekhah, et al., "Made-to-order metal-organic frameworks for trace carbon dioxide removal and air capture", Nature Communications, Jun. 25, 2014, 1-7.

Shekhah, et al., "MOF thin films: existing and future applications", Chem. Soc. Rev. 2011, 40, 1081-1106.

Shekhah, et al., "Step-by-Step Route for the Synthesis of Metal-Organic Frameworks", J. Am. Chem. Soc., 2007, 2 pages.

Shekhah, et al., "The liquid phase epitaxy method for the construction of oriented ZIF-8 thin films with controlled growth on functionalized surfaces", Chem. Commun., 2013, 49, 10079.

Shi, et al., "Synthesis of MIL-100(Fe) at Low Temperature and Atmospheric Pressure", Journal of Chemistry, vol. 12, No. 32, Jan. 1, 2013, 5878-4.

Takamizawa, et al., "Single-Crystal Membrane for Anisotropic and Efficient Gas Permeation", Journal of the American Chemical Society 2010 132 (9), 2862-2863.

Yang, et al., "Hydrothermal synthesis and characterization of a series of luminescent Zn(ii) and Cd(ii) coordination polymers with the new versatile m ultidentate ligand 1,3-di(1,2,4-triazol-4-yl)benzene", Crystengcomm, vol. 15, No. 40, Jan. 1, 2013, 8097.

Zacher, et al., "Thin films of metal—organic frameworks", Chem. Soc. Rev., 2009, 38, 1418-1429.

Zhou, et al., "Introduction to Metal—Organic Frameworks", Chem. Rev. 2012, 112, 673-674.

GREEN METHODS FOR PREPARING HIGHLY CO2 SELECTIVE AND H2S TOLERANT METAL ORGANIC FRAMEWORKS

BACKGROUND

Restricted energy and materials resources, combined with the growing fears from various undesirable industrial byproducts, has increased incentives for developing new, cleaner and more efficient synthetic methodologies to aid the chemical industry in handling the global problems of pollution, growing energy demand and the shortage of raw materials. Metal organic frameworks (MOFs) are very attractive materials due to their large porosity, tunability in composition and topology, in addition to huge potentials of their use in fields such as catalysis, gas storage, gas sensing, greenhouse gases emissions control and many other separations. These promising hybrid porous solids are typically synthesized using solvo/hydrothermal routes. Other methods have also been proposed, including microwave-assisted solvothermal methods; microfluidics; ionic liquids; and electro-chemistry, which are all based on synthesis of MOFs in solutions.

However, these synthetic methodologies have proven to be of interest only for lab-scale research and have been minimally implemented at pilot or larger industrial scales. In addition to often being economically impracticable, the above-mentioned solution-based synthesis methodologies for MOFs suffer from the need to use toxic and/or corrosive metal salt reagents and generate acid byproducts. Recently, solvent-free methodologies use to prepare different MOFs, such as ZIF-8, MIL-100, and other analogues, were recently reported. However, these methodologies are not yet scalable, and are therefore limited to research applications. Pilot and industrial scale production of MOFs requires consideration of a number of aspects including scientific practicability, environmental friendliness, efficiency, and capital and manufacturing costs. These factors are not being suitably achieved by current MOF manufacturing methods. Accordingly, solvent-free and/or green synthesis methods which are scalable to an industrial level are greatly needed.

SUMMARY

In general, this disclosure describes green synthesis of MOFs. In particular, this disclosure describes green synthesis of SIFSIX-n-M MOF analogues. It should be noted that although the synthesis techniques of this disclosure are described with respect to SIFSIX-n-M MOF analogues, such techniques are generally applicable to many other MOFs as will be readily apparent to those of skill in the art after review of this disclosure.

According to one example of this disclosure, a green synthesis method for synthesizing a MOF comprises mixing a metal precursor with a ligand precursor to form a mixture; adding water to the mixture; heating the mixture at a first temperature after the water is added to the mixture; heating the mixture to a second temperature; and isolating a three-dimensional metal organic framework structure.

According to another example of this disclosure, a green synthesis method for synthesizing a MOF comprises mixing a metal precursor with a ligand precursor to form a mixture; adding water to the mixture; heating the mixture at a first temperature after the water is added to the mixture; and isolating a two-dimensional metal organic framework intermediate structure.

The details of one or more examples are set forth in the accompanying drawings and the description below. Other features, objects, and advantages will be apparent from the description and drawings, and from the claims.

DETAILED DESCRIPTION

Figure 1A:
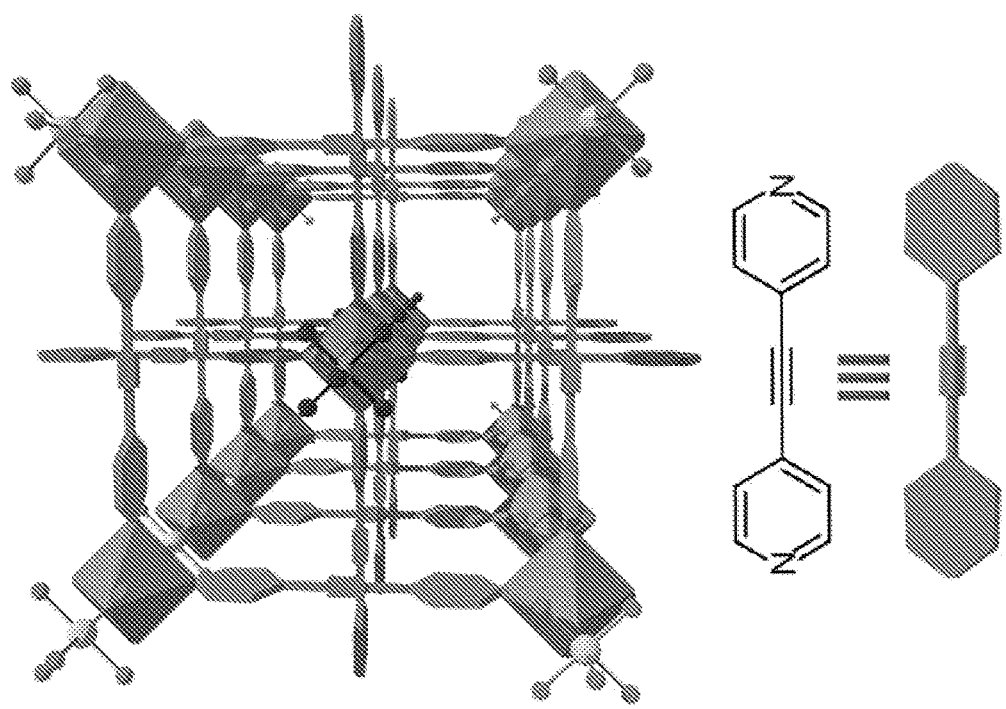
FIG. 1A illustrates a perspective view of a SIFSIX-n-M MOF coordinated by dipryidilacetylene ligands, according to an embodiment of the disclosure.

The disclosure herein provides green-synthesis methods for synthesizing porous materials, which reduce or eliminate the need for solvents and corrosive metal salt reagents, reduce or eliminate toxic and/or acidic byproducts, and are scalable to industrial levels. The methods disclosed herein are generally applicable to materials comprising a porous network constructed from the assembly of molecular building blocks (MBBs). A porous network can include Porous Organic Polymer (POP), Covalent-Organic Framework (COF), Porous Aromatic Framework (PAF), Porous Polymer Network (PPN), Conjugated Microporous Polymers (CMP), Microporous Polymer Network (MPN), Polymer with Intrinsic Microporosity (PIM), Hyper Crossed-linked Polymer (HCP), Metal-organic Framework (MOF), Coordination Polymers (CP), Porous Coordination Polymers (PCP), Porous Coordination Networks (PCN), or Metal-Organic Materials (MOM), or a mixture thereof. POP, PAF, COF, PPN, CMP, MPN, PIM, HCP are all included in the term porous organic polymer (POP); MOF, CP, PCP, PCN, MOM are all included in the term metal-organic framework (MOF). These materials are promising due to their ideal intrinsic properties including high porosity (e.g., up to 6000

$m^2 \cdot g^{-1}$), high chemical and thermal stability, and structural and functional tunability, among others. Specific topologies can be targeted through the careful choice of MBBs and synthetic conditions to afford crystalline materials, but such a control of topology and crystallinity is not mandatory for the control of porosity in POPs.

Metal organic frameworks (MOFs) are a versatile and promising class of crystalline solid state materials which allow porosity and functionality to be tailored towards various applications. MOF crystal chemistry uses a molecular building block (MBB) approach that offers potential to construct MOFs where desired structural and geometrical information are incorporated into the building blocks prior to the assembly process.

Generally, MOFs comprise a network of nodes and ligands, wherein a node has a connectivity capability at three or more functional sites, and a ligand has a connectivity capability at two functional sites each of which connect to a node. Nodes are typically metal ions or metal containing clusters, and, in some instances, ligands with node connectivity capability at three or more functional sites can also be characterized as nodes. In some instances, ligands can include two functional sites capable of each connecting to a node, and optionally one or more additional functional sites which do not connect to nodes within a particular framework. In some embodiments, ligands can be poly-functional, or polytopic, and comprise two or more functional sites capable of each connecting to a node. In some embodiments, polytopic ligands can be heteropolytopic, wherein at least two of the two or more functional sites are different.

A MBB can comprise a metal-based node and an organic ligand which extrapolate to form a coordination network. Such coordination networks have advantageous crystalline and porous characteristics affecting structural integrity and interaction with foreign species (e.g., gases). The particular combination of nodes and ligands within a framework will dictate the framework topology and functionality. Through ligand modification or functionalization, the environment in the internal pores can be modified to suit specific applications.

Generally, a MBB, or a network of MBBs, can be represented by the formula [(node)a(ligand)b(solvent)c]n, wherein n represents the number of molecular building blocks. Solvent represents a guest molecule occupying pores within the MOF, for example as a result of MOF synthesis, and can be evacuated after synthesis to provide a MOF with unoccupied pores. Accordingly, the value of c can vary down to zero, without changing the definitional framework of the MOF. Therefore, in many instances, MOFs as provided herein can be defined as [(node)a(ligand)b]n, without reference to a solvent or guest molecule component.

Figure 1B:
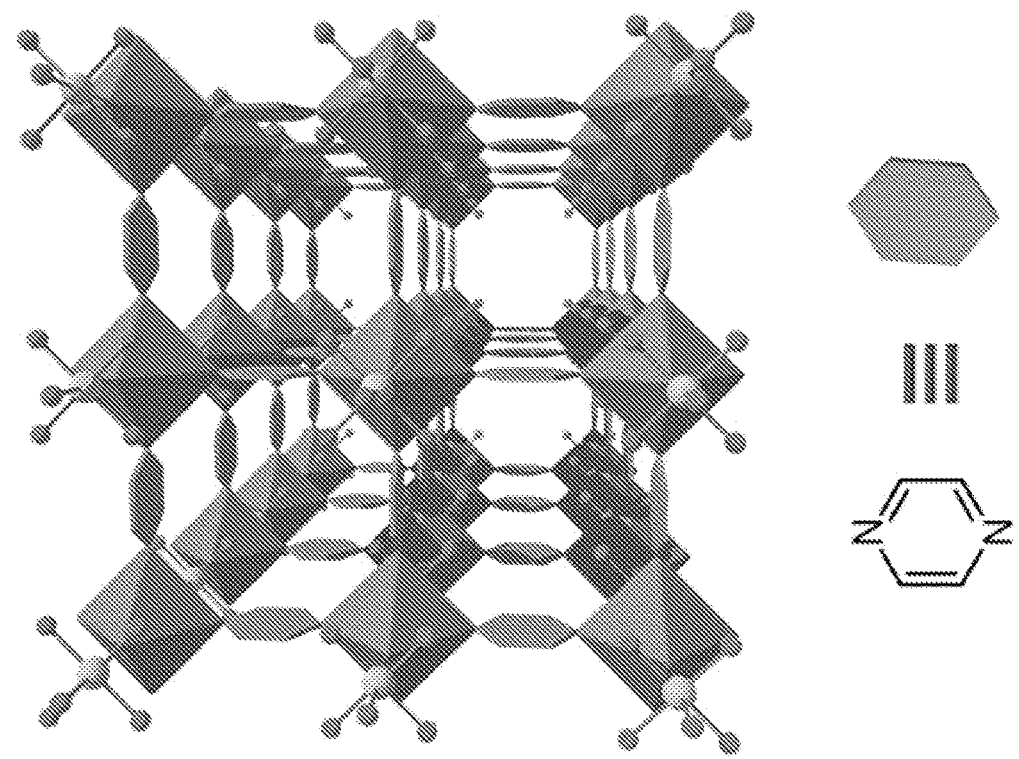
FIG. 1B illustrates a SIFSIX-n-M MOF coordinated by pyrazine ligands, according to an embodiment of the disclosure.

An example of a class of MOFs is SIFSIX-n-M, wherein n is at least two, and M can comprise Ni, Cu. Zn, Fe, or Co. More specifically, the M can comprise Ni. The SIFSIX-n-M MOF class is isoreticular across its metal analogues (i.e., each M analogue has the same framework topology) and is characterized by periodically arrayed hexafluorosilicate (SIFSIX) pillars. SIFSIX-n-M MOFs have many desirable characteristics, including tunable pore sizes, which lend the various analogues well to a number of industrial applications. FIGS. 1A-B show examples of SIFSIX-n-MOF analogues. FIG. 1A shows a SIFSIX-n-M MOF coordinated by dipryidilacetylene (DPA) ligands. A specific analogue of this MOF is SIFSIX-2-Cu, among others. FIG. 1B shows a SIFSIX-n-M MOF coordinated by pyrazine ligands. Specific analogues of this MOF include SIFSIX-3-Cu, SIFSIX-3-Zn, and SIFSIX-3-Ni, among others.

SIFSIX-n-M MOFs can be coordinated by a variety of organic ligands. In some embodiments, the ligand can be any bi-functional N-donor linkers based on monocyclic or polycyclic group (aromatic or not). In some embodiments, a ligand can comprise a polydentate, or poly-functional ligand, such as a bi-functional ligand, a tri-functional ligand, or ligands with four or more functional sites. In some embodiments, a ligand can comprise an N-donor linker. In some embodiments a ligand can comprise a poly-functional ligand. In some embodiments, a ligand can comprise a plurality of N-donor functional groups. Pyrazine is an example of a ligand with two N-donor functional groups. In some embodiments, a ligand can comprise a monocyclic or polycyclic group structure, wherein the cyclic groups can be aromatic or nonaromatic. In some embodiments, a ligand can comprise a nitrogen-containing monocyclic or polycyclic group structure. In some embodiments, a ligand can comprise a nitrogen-containing heterocyclic ligand, including pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), 1,2-bis(4-pyridyl)acetylene (dpa), and tautomers thereof.

In particular, SIFSIX-n-M MOFs are suitable for $CO_2$ removal applications, due to their strong $CO_2$ adsorption sites, including pre-combustion $CO_2$ capture, and post-combustion $CO_2$ capture, and natural gas and biogas upgrading. SIFSIX MOF materials exhibit very high (non-reactive) $CO_2$ energetics, but fully reversible physical driven adsorption-desorption operations at very mild conditions. The ideal combination of contracted pore size and the high charge density also provide high $CO_2$ adsorption selectivity over $H_2$, $CH_4$ and $N_2$ across a wide range of $CO_2$ concentrations. While SIFSIX MOFs have been synthesized in the lab, production-scale SIFSIX synthesis methods must be developed in order to lend industrial utility to these materials.

As discussed above, MOFs are typically synthesized using solvo/hydrothermal methods. Solvo/hydrothermal methods used for synthesizing SIFSIX-n-M MOFs generally include forming a first solution by mixing a metal precursor with a solvent, wherein the metal precursor includes an M-$SiF_6$ moiety, and forming a second solution by mixing a ligand precursor with a solvent. The molar ratio of the ligand precursor to the metal precursor can be about 3:1 to about 6:1. Methanol is a suitable solvent, among others. Next, one of the two mixtures is layered onto the other, whereupon a MOF is allowed to form for a period of time. Layering can be done in a glass tube. The period of time can be 24 hours, for example. The MOF can be then washed with a solvent, and optionally further heated and/or dried to remove solvent guest molecules.

The future deployment of MOF materials at the larger scale for many applications such as adsorbents, catalysts, and sensors, among many others, require clean, environmentally friendly, easy, cost efficient and scalable synthesis procedures. Solution-based MOF synthesis methodologies, such as the solvo/hydrothermal method previously discussed, suffer from the need to use toxic and/or corrosive metal salts reagents. In addition to being costly and hazardous, these reagents further generate acid byproducts which are often susceptible to solvolysis and require costly disposal. The need for fresh solvents, enhanced safety precautions, and waste disposal greatly increases both the capital costs and production costs of these methods. Low reproducibility further precludes industrial applications of solvo/hydrothermal synthesis methods. Accordingly, the reproducible, solvent-free route, green MOF synthesis methods described herein show great promise for scalable applications at pilot and industrial levels which avoid toxic and corrosive metal salts and external bases.

Figure 2A:
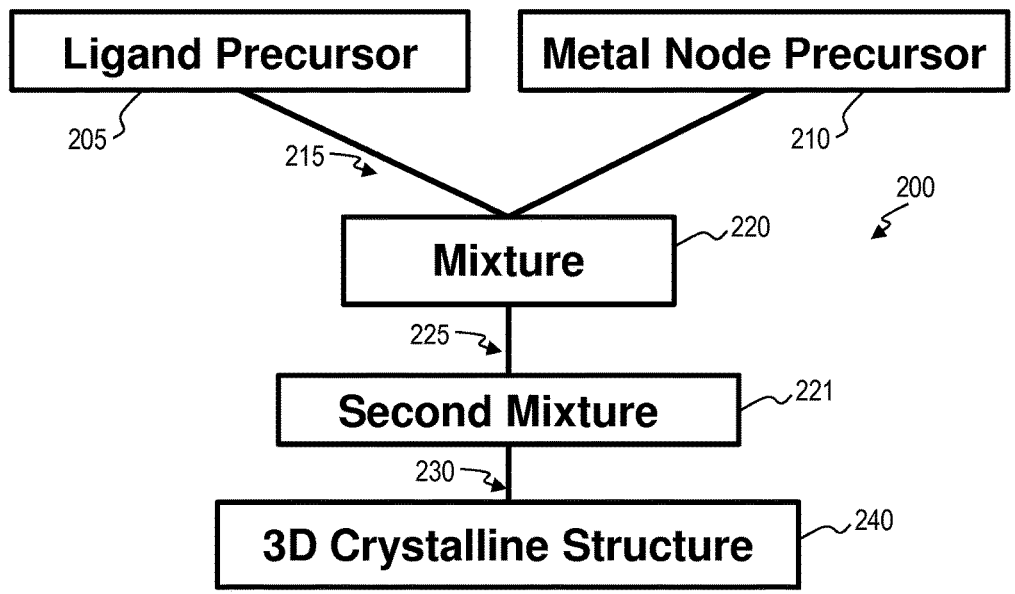
FIGS. 2A-B illustrate schematic representations of green metal organic framework synthesis methods, according to one or more embodiments of the disclosure.

FIG. 2A illustrates a schematic representation of a green MOF synthesis method 200, comprising mixing 215 a ligand precursor 205 with a metal node precursor 210 to form a solvent-free mixture 220. A solvent can include any known chemical solvent, such as methanol. As used herein, "solvent" does not refer to water. The ligand precursor 205 can be mixed with the metal node precursor 210 in a stoichiometric ratio. The ligand precursor 205 can be mixed with the metal node precursor 210 wherein the ligand precursor 205 is in stoichiometric excess. The ligand precursor 205 can be mixed with the metal node precursor 210 wherein the metal node precursor 210 is in stoichiometric excess. Mixing 215 can comprise mechanical mixing, such as stirring or agitating. Mixing 215 can further comprise grinding, wherein one or more of the ligand precursor 205 and the metal node precursor 210 are reduced in size. Mixing 215 can optionally comprise heating caused by friction between the ligand precursor 205 and the metal node precursor 210 during mixing 215. The mixture 220 can optionally be wetted with water during mixing 215 to reduce friction-induced heating and/or encourage contact between the ligand precursor 205 and the metal node precursor 210. After mixing 215, the mixture 220 is wetted 225 with water to form a second mixture 221. In some embodiments, after wetting 225, an amorphous (i.e., minimal crystallinity) intermediate product can be formed, although formation of such an intermediate is not essential to the practice of method 200. After wetting 225, the mixture 220 can be heated 230 at a temperature for a period of time to form a 3D crystalline structure 240. The temperature during heating 230 may not necessarily describe the temperature of the mixture 220 during heating. Heating 230 can optionally occur in a closed vessel. The closed vessel can be isochoric.

Figure 2B:
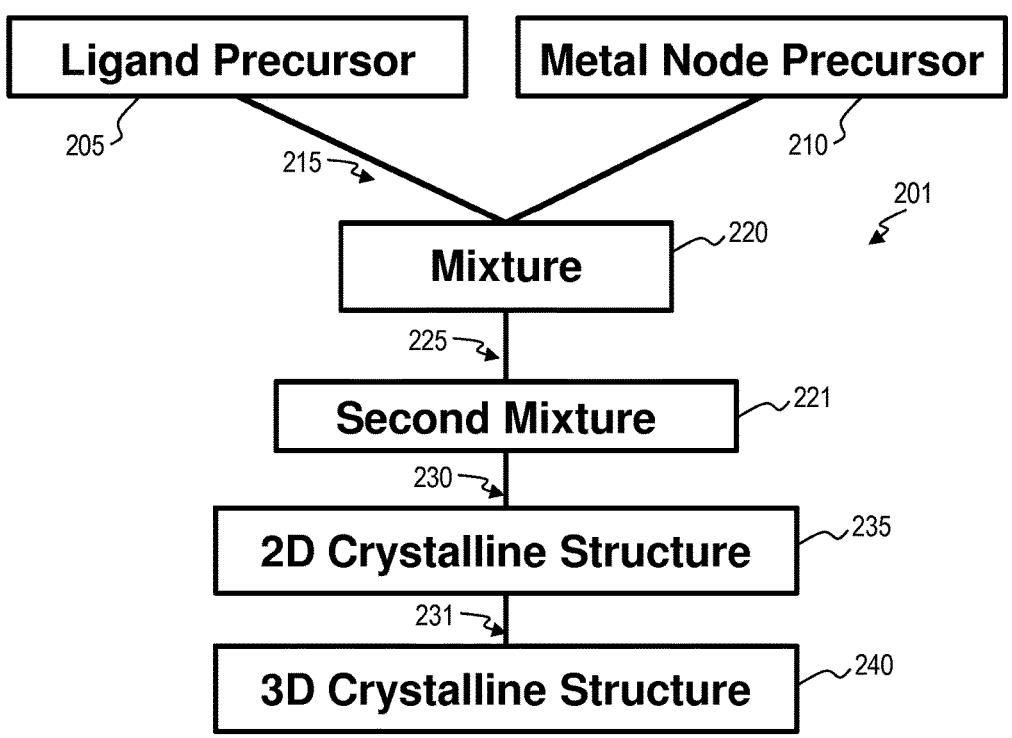

FIG. 2B illustrates a schematic representation of a green MOF synthesis method 201, comprising mechanically mixing 215 a ligand precursor 205 with a metal node precursor 210 to form a mixture 220. The ligand precursor 205 can be mixed with the metal node precursor 210 in a stoichiometric ratio. The ligand precursor 205 can be mixed with the metal node precursor 210 wherein the ligand precursor 205 is in stoichiometric excess. The ligand precursor 205 can be mixed with the metal node precursor 210 wherein the metal node precursor 210 is in stoichiometric excess. Mixing 215 can comprise mechanical mixing, such as stirring or agitating. Mixing 215 can further comprise grinding, wherein one or more of the ligand precursor 205 and the metal node precursor 210 are reduced in size. Mixing 215 can optionally comprise heating caused by friction between the ligand precursor 205 and the metal node precursor 210 during mixing 215. The mixture 220 can optionally be wetted with water during mixing 215 to reduce friction-induced heating and/or encourage contact between the ligand precursor 205 and the metal node precursor 210. After mixing 215, the mixture 220 is wetted 225 with water to form a second mixture 221. In some embodiments, after wetting 225, an amorphous (i.e., minimal crystallinity) intermediate product can be formed, although formation of such an intermediate is not essential to the practice of method 200. After wetting 225, the mixture 220 can be heated 230 at a first temperature for a first period of time to form a 2D crystalline structure 235. The temperature during heating 230 may not necessarily describe the temperature of the mixture 220 during heating. Heating 230 can optionally occur in a closed vessel. The closed vessel can be isochoric. The 2D crystalline structure 235 can then be heated 231 at a second temperature for a second period of time to effect a phase change and form a 3D crystalline structure 240. Heating 231 can occur in an open or closed vessel. The second temperature can be higher than the first temperature.

Green synthesis methods 200 and 201 can be described as mechanosynthesis methods, and can be advantageous where one or both of the ligand precursor 205 and the metal node precursor 210 have low solubility in solvents and/or water. Further, green synthesis methods 200 and 201 can yield crystalline MOF structures much more quickly than with conventional solvo/hydrothermal methods. In preparing SIFSIX-n-M MOF structures using methods 200 and 201, metal node precursors 210 can include $NiSiF_6$, $CuSiF_6$, $ZnSiF_6$, $CoSiF_6$, or $FeSiF_6$. In some embodiments wherein SIFSIX-n-M MOF structures are prepared using methods 200 and 201, metal node precursors 210 can include $NiSiF_6$, $CoSiF_6$, or $FeSiF_6$. SIFSIX-n-M MOF 2D and/or 3D structures prepared using methods 200 and 201 can be suitable for use in gas separation and purification. For example, SIFSIX-n-M MOF 2D and/or 3D structures prepared using methods 200 and 201 can be used for $CO_2$ sequestration. Further, SIFSIX-n-M MOF 2D and/or 3D structures prepared using methods 200 and 201 can be $H_2S$ tolerant. A structure which is tolerant to $H_2S$ does not lose structural integrity after contacting or adsorbing or absorbing $H_2S$, nor lose sorption capability for other chemical species after contacting or adsorbing or absorbing $H_2S$. For example, an MOF which is tolerant to $H_2S$ can adsorb and desorb $CO_2$ from a gaseous stream containing $H_2S$ over a number of sorption cycles without any substantial degradation of sorption performance resulting from contact with the $H_2S$ in the gaseous stream.

Ligand precursors 205 can include any bi-functional N-donor linkers based on monocyclic or polycyclic group (aromatic or not). In some embodiments, a ligand precursor 205 can comprise a polydentate, or poly-functional ligand, such as a bi-functional ligand, a tri-functional ligand, or ligands with four or more functional sites. In some embodiments, a ligand can comprise an N-donor linker. In some embodiments a ligand precursor 205 can comprise a polyfunctional ligand. In some embodiments, a ligand precursor 205 can comprise a plurality of N-donor functional groups. In some embodiments, a ligand precursor 205 can comprise a monocyclic or polycyclic group structure, wherein the cyclic groups can be aromatic or nonaromatic. In some embodiments, a ligand precursor 205 can comprise a nitrogen-containing monocyclic or polycyclic group structure. In some embodiments, a ligand precursor 205 can comprise a nitrogen-containing heterocyclic ligand, including pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), 1,2-bis(4-pyridyl)acetylene (dpa), and tautomers thereof.

In preparing SIFSIX-n-M MOF structures using methods 200 and 201, heating 230 can occur at temperatures up to about 45° C., up to about 50° C., up to about 55° C., up to about 60° C., up to about 65° C., up to about 70° C., up to about 75° C., or above about 75° C. Heating 230 can occur for up to about 2.5 hours, up to about 3 hours, up to about 3.5 hours, up to about 4 hours, up to about 4.5 hours, up to about 5 hours, up to about 5.5 hours, or above about 5.5 hours. In preparing SIFSIX-n-M MOF structures using method 201, heating 231 can occur at temperatures up to about 90° C., up to about 95° C., up to about 100° C., up to about 105° C., up to about 110° C., up to about 115° C., up to about 120° C., or above about 125° C. Heating 231 can occur at temperatures at least above 100° C., or at temperatures at least above 105° C. Heating 230 can occur for up to about 2.5 hours, up to about 3 hours, up to about 3.5 hours, up to about 4 hours, up to about 4.5 hours, up to about 5 hours, up to about 5.5 hours, or above about 5.5 hours.

2D and 3D SIFSIX-n-M MOF structures prepared using methods 200 and 201 can include SIFSIX-2-Cu, SIFSIX-3-Cu, SIFSIX-3-Zn, SIFSIX-3-Ni, SIFSIX-3-Co, SIFSIX-3-Fe. In one embodiment, the SIFSIX-n-M MOF structures prepared is SIFSIX-3-Ni. Further, SIFSIX-n-M MOFs can be prepared using methods 200 and/or 201 which exhibit the same structural and functional properties as the corresponding SIFSIX-n-M MOFs prepared solvo/hydrothermally. For example, SIFSIX-n-M MOFs prepared using the green-synthesis methods herein can be used as separation agents for effective $CO_2$ capture/removal from various sources. This technology is technically and economically viable for scale-up and commercialization. The green chemistry for SIFSIX-n-M MOF materials can be a solid bridge to next stage of implementation in real applications such as post-combustion, direct air capture and traces $CO_2$ removal.

Example 1A: Synthesis of SIFSIX-3-Ni ($C_8N_4H_8NiSiF_6$) Prepared Solvothermally A methanol solution (5.0 mL) of pyrazine (pyz, 0.30 g, 3.0 mmol) was layered in a glass tube onto a methanol solution (5.0 mL) of $NiSiF_6.xH_2O$ (0.325 g, 0.6 mmol). Upon layering, a slow formation of light blue powder was observed, and the powder was left for 24 hours in the mother solution. The powder was then collected and washed extensively with methanol then dried at 105° C. under vacuum.

Figure 3:
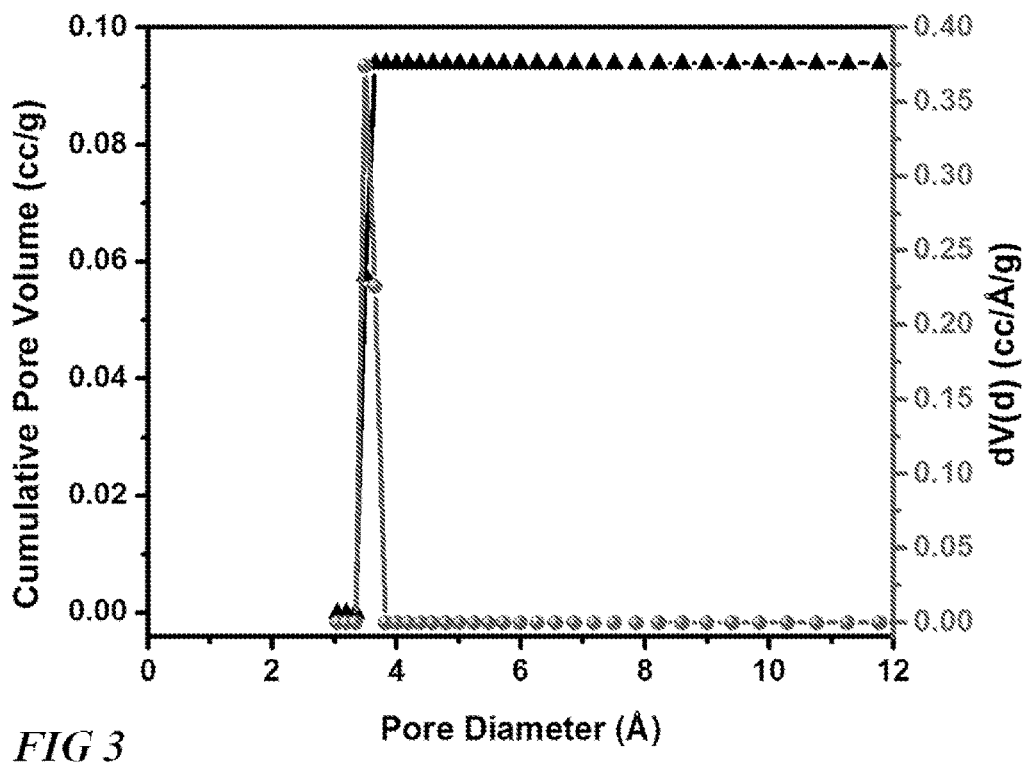
FIG. 3 illustrates pore size distribution from $CO_2$ sorption isotherms at 77 K for a metal organic framework, according to one or more embodiments of the disclosure.

The solvothermally synthesized SIFSIX-3-Ni structure exhibited a unit cell size of 378 Å3, and an average pore size of 3.8 Å as shown in FIG. 3 which illustrates pore size distribution from $CO_2$ sorption isotherms at 77 K. The SIFSIX-3-Ni structure comprised a denser unit cell configuration than the Zn SIFSIX analogue, which has an average pore size of about 3.5-4 Å and a unit cell size of about 378 Å3, possibly attributed to the stronger bonding between the Ni(II) and pyrazine as compared to Zn. The Cu SIFSIX analogue conversely had a lower average pore size than the SIFSIX-3-Ni structure of about 3.5 Å, similarly suggesting stronger bonding between the Cu and pyrazine as compared to Ni.

Figure 4A:
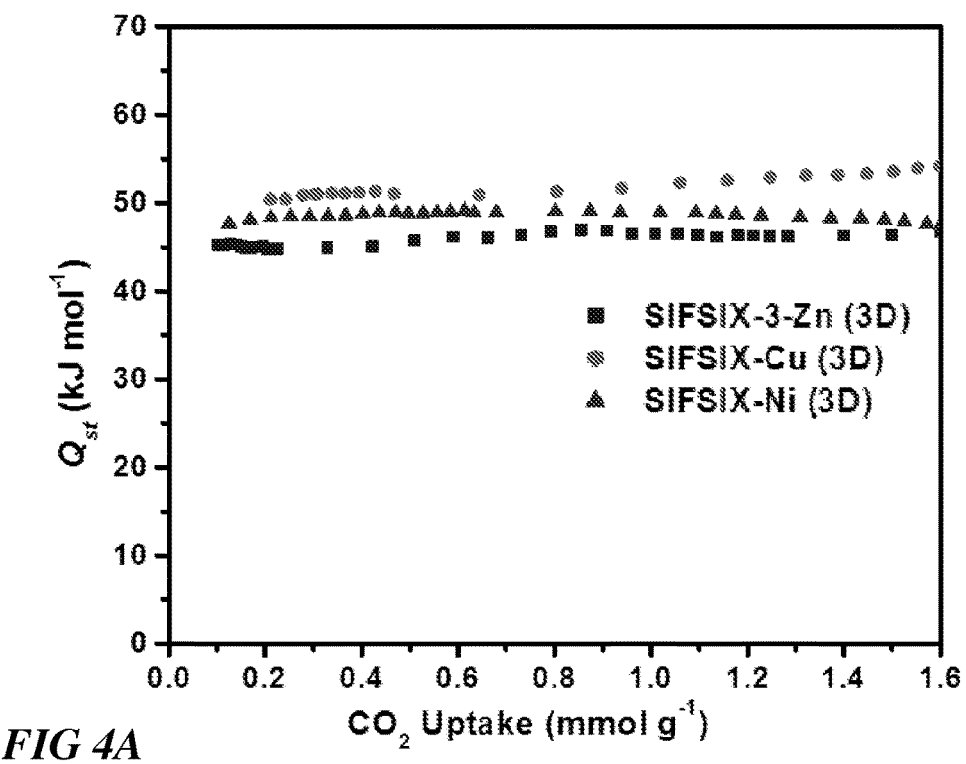
FIG. 4A shows isosteric heats of adsorption at low coverage for SIFSIX-Cu-3, SIFSIX-3-Zn and SIFSIX-3-Ni metal organic frameworks, according to one or more embodiments of the disclosure.
Figure 4B:
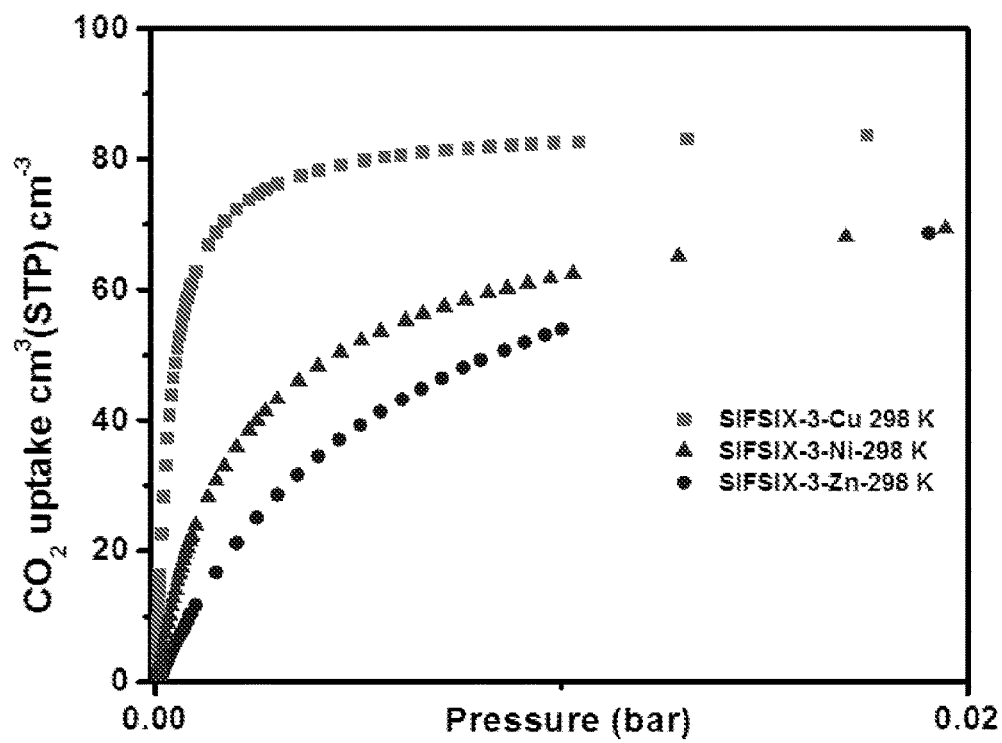
FIG. 4B shows $CO_2$ adsorption isotherms for SIFSIX-Cu-3, SIFSIX-3-Zn and SIFSIX-3-Ni metal organic frameworks, according to one or more embodiments of the disclosure.

The smaller/larger unit cell of the Ni analogue as compared to the Zn and Cu analogues, respectively, is further confirmed by the respective heat of adsorptions shown in FIG. 4A. The Qst of $CO_2$ adsorption is an intrinsic property that dictates the affinity of the pore surface toward $CO_2$, which in turn plays a major role in determining the adsorption selectivity and the necessary energy to release $CO_2$ during the regeneration step. The Qst for $CO_2$ is in the range of fully reversible $CO_2$ adsorption (30-50 kJ mol-1), in agreement with the full evacuation of SIFSIX-3-Ni at 298-223K in vacuum. For SIFSIX-3-Zn and SIFSIX-3-Cu, the Qst for $CO_2$ adsorption was relatively constant up to high $CO_2$ loadings indicating homogenous binding sites over the full range of $CO_2$ loading. Specifically, the Qst of $CO_2$ adsorption for SIFSIX-3-Ni was 8% and 6% higher/lower (48 kJ mol-1) than the Zn and the Cu analogues, respectively. $CO_2$ adsorption isotherms for the Ni, Cu, and Zn analogues are shown in FIG. 4B. The high selectivity toward $CO_2$ in case of SIFSIX-3-Ni is driven by the unique optimal combination between thermodynamics and kinetics (i.e., the occurrence of strong/homogenous $CO_2$ interaction and relatively fast $CO_2$ adsorption).

Figure 5A:
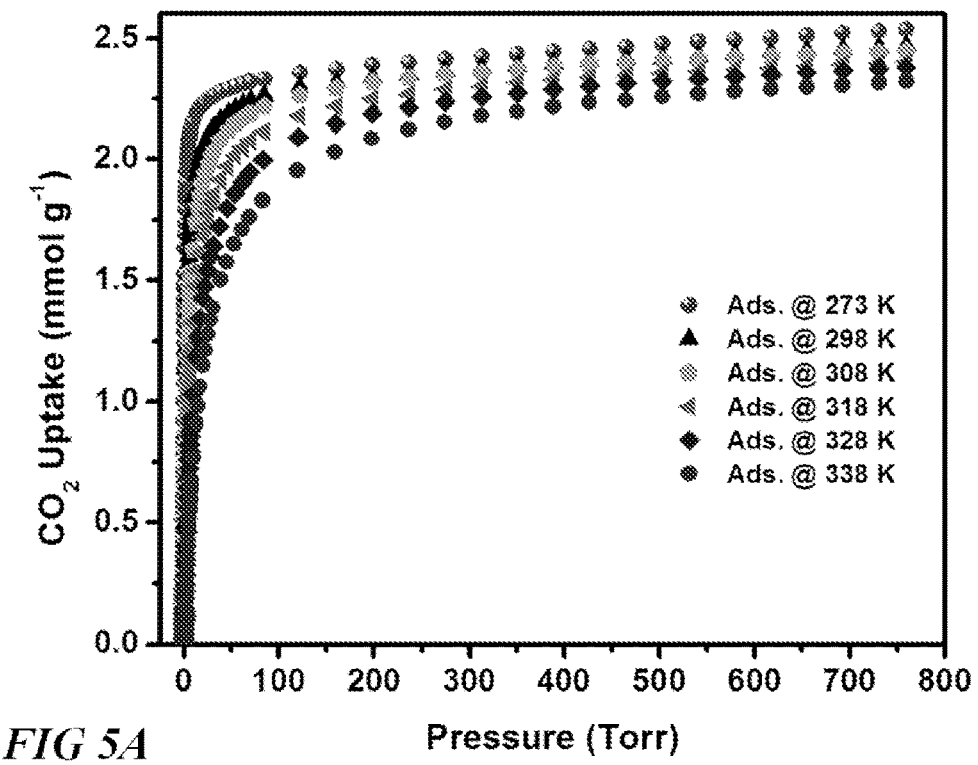
FIG. 5A shows variable temperature adsorption isotherms of $CO_2$ for a SIFSIX-3-Ni metal organic frameworks, according to one or more embodiments of the disclosure.
Figure 5B:
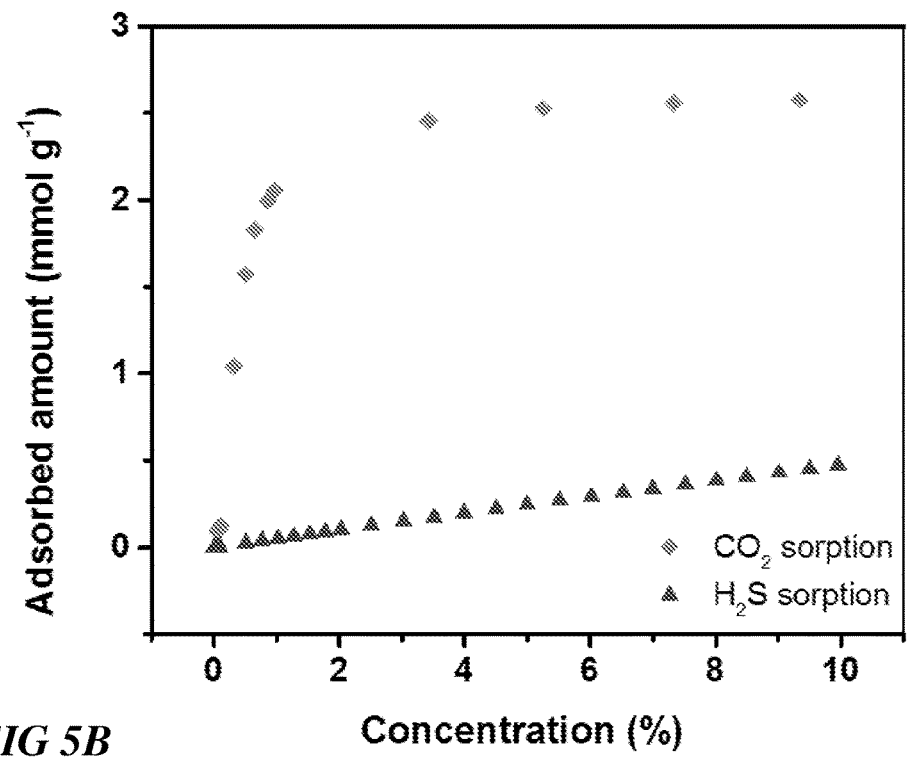
FIG. 5B shows $CO_2$ and $H_2S$ sorption isotherms for a SIFSIX-3-Ni metal organic frameworks, according to one or more embodiments of the disclosure.

Further, the SIFSIX-3-Ni structure exhibited reversible $CO_2$ sorption and structural stability in the presence of H2S. FIG. 5A shows variable temperature adsorption isotherms of $CO_2$ for SIFSIX-3-Ni. FIG. 5B shows $CO_2$ and $H_2S$ sorption isotherms for SIFSIX-3-Ni. $H_2S$ uptake remains same after repeated sorption and activation cycles. $H_2S$ sorption isotherms were collected on the SIFSIX-3-Ni sample, showing an uptake of around 1.3 mol·g−1 of $H_2S$ at 10% concentration. Reversibility and stability of the sample was confirmed after repeating $H_2S$ sorption and recording identical $H_2S$ isotherms. Based on these studies, it is confirmed that the green-synthesis method for SIFSIX MOFs can deliver stable MOF architectures which are tolerant to $H_2S$, able to be readily and reliably regenerated/recycled, and suitable for a number of industrial applications such as $CO_2$ separation from $N_2$, $O_2$, $CH_4$ and H2 containing mixtures.

Example 1B: SIFSIX-3-Ni Green Route Synthesis

Figure 6A:
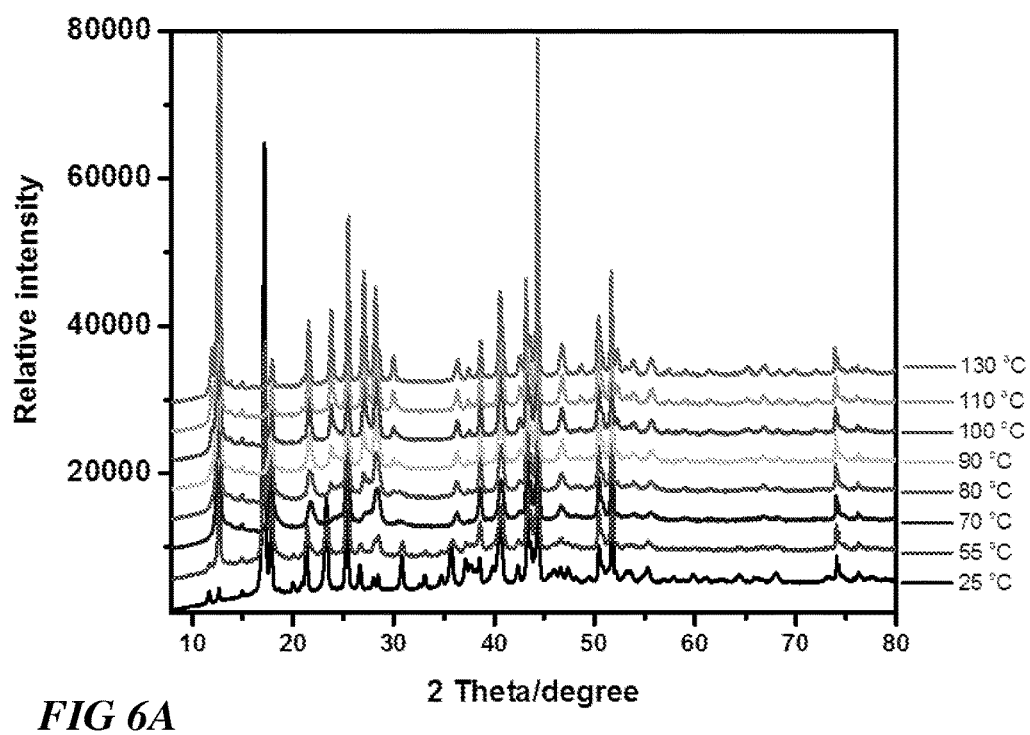
FIG. 6A shows a variable temperature PXRD of the SIFSIX-3-Ni metal organic frameworks, according to one or more embodiments of the disclosure.

SIFSIX-3-Ni can be synthesized through a green synthesis route. This facile methodology is based first on mechanically mixing both of the solid precursors i.e. the pyrazine and the $NiSiF_6$ with a molar ratio of 5:1 respectively, followed by a wetting procedure with few drops of water followed by careful heating. A solid mixture of pyrazine (pyz, 0.30 g, 3.0 mmol) and $NiSiF_6.xH_2O$ (0.325 g, 0.6 mmol) was mechanically ground together and then wetted with few drops of water, yielding an amorphous product with low crystallinity. The product was then heated up to 65° C. in a closed vial for 4 hours, whereupon a color change to light violet was observed. The colour change is associated with the formation of a 2D SIFSIX-3-3Ni structure (i.e., crystallisation of ($NiSiF_6(pyz) (H_2O)_2$)), which is the Ni analogue of the 2D ($CuSiF_6(pyz) (H_2O)_2$). The powder was then heated at 105° C. for another 4 hours whereupon a light blue powder was formed, indicating a structural transformation. FIG. 6A shows the variable temperature PXRD of the SIFSIX-3-Ni analogue starting from 25° C., which shows the phase transformation from a 2D Ni structure to the NiSIFIX-3-Ni 3D structure, starting at about 55° C. and completing at about 70° C. Upon further heating the PXRD signal of the SIFSIX-3-Ni starts to become more intense and the Ni analogue shows high stability up to 130° C. The change in phase is also accompanied by a change in the color from a light violet color to a light blue color upon full conversion.

Figure 6B:
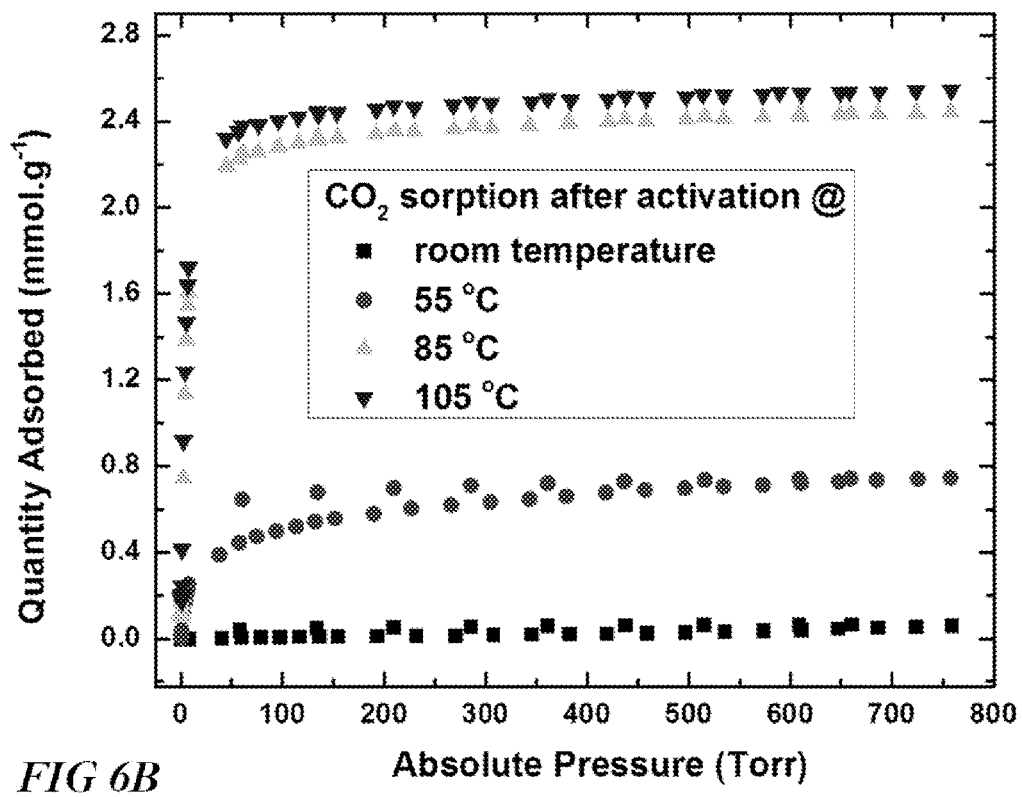
FIG. 6B shows $CO_2$ adsorption isotherms at 298 K for a SIFSIX-3-Ni metal organic frameworks, according to one or more embodiments of the disclosure.
Figure 6C:
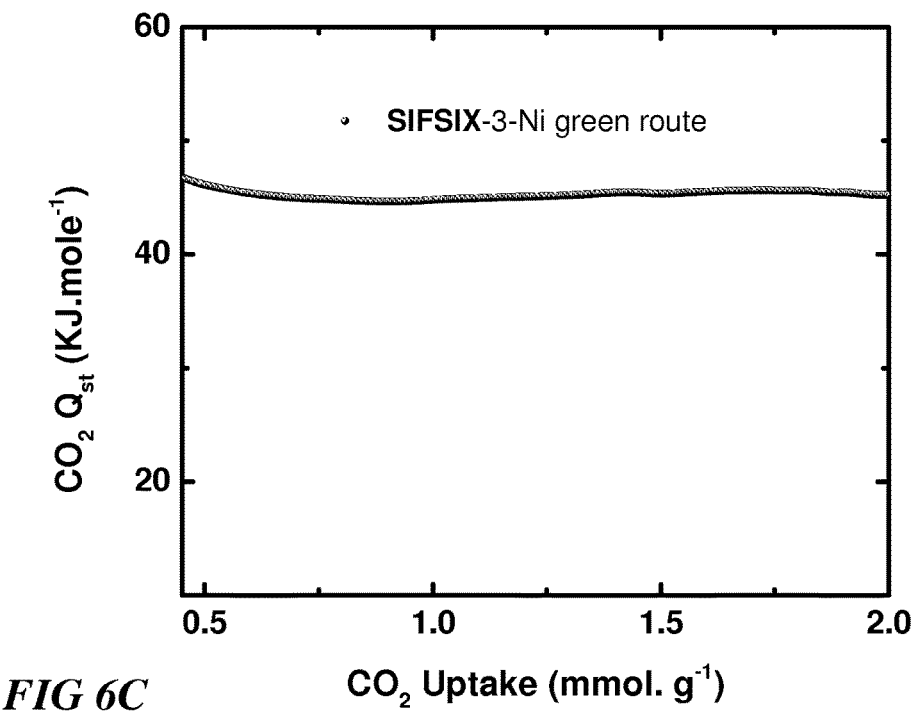
FIG. 6C shows isosteric heats of adsorption at low coverage for a SIFSIX-Ni-3 metal organic frameworks, according to one or more embodiments of the disclosure.

The PXRD diagram of the material prepared using the green route method described above was found to match the SIFSIX-3-Ni-3D structure prepared using the solovothermal method described in Example 1A. Further, the Ni analogue prepared by the green route in this Example showed the same variable temperature adsorption isotherms at low pressure as the Ni analogue prepared by the solvothermal method described in Example 1A, which supports the similarity of the 3D SIFSIX-3-Ni structures made with both approaches. FIG. 6B shows $CO_2$ adsorption isotherms at 298 K which illustrate the change in the $CO_2$ uptake with the change in the activation temperature for the adsorption SIFSIX-3-Ni analogue prepared by the green route method. The $CO_2$ uptake shows an increase in the $CO_2$ uptake with increasing the activation temperature, and similar optimal $CO_2$ adsorption isotherm is obtained after activation at 105° C., as compared to the optimal $CO_2$ adsorption isotherms shown in FIG. 5A. Sorption behavior can be correlated with the phase change observed during synthesis and the complete conversion to a 3D-structure. The Qst for $CO_2$ was also found in good correlation with SIFSIX-3-Ni prepared solvothermally, as shown in FIG. 6C.

Example 2A: SIFSIX-2-Cu Green Route Synthesis

A trial was conducted using a similar experimental procedure to that of Example 1B, using a copper metal precursor in place of the nickel metal precursor. Promising results were not immediately achieved.

Example 2B: SIFSIX-3-Cu Green Route Synthesis

A trial was conducted using a similar experimental procedure to that of Example 1B, using a copper metal precursor in place of the nickel metal precursor. Promising results were not immediately achieved.

Example 2C: SIFSIX-3-Zn Green Route Synthesis

A trial was conducted using a similar experimental procedure to that of Example 1B, using a zinc metal precursor in place of the nickel metal precursor. Promising results were not immediately achieved.

What is claimed is:

1. A method for preparing a metal organic framework comprising:
    mixing a solid metal precursor with a solid ligand precursor to form a mixture of the solid precursors, wherein the solid metal precursor includes $M-SiF_6$, wherein M includes a metal;
    wetting the mixture of the solid precursors with one or more drops of water; and
    heating the wetted mixture at a first temperature to obtain a two-dimensional metal organic framework intermediate structure.

2. The method of claim 1, wherein the metal of the solid metal precursor is selected from a group consisting of Ni, Cu, Zn, Fe, and Co.

3. The method of claim 1, wherein the metal includes Ni.

4. The method of claim 1, wherein the solid ligand precursor includes pyrazine, 4,4'-Bipyridin, 1,4-Diazabicyclo[2.2.2]octane, or 1,2-bis(4-pyridyl)acetylene.

5. The method of claim 1, wherein the solid ligand precursor includes a nitrogen-containing heterocyclic ligand.

6. The method of claim 1, wherein the molar ratio of the solid ligand precursor to the metal precursor is about 3:1 to about 6:1.

7. The method of claim 1, further comprising forming SIFSIX-Ni-3 metal organic framework.

8. The method of claim 1, wherein the two-dimensional metal organic framework intermediate structure is $H_2S$ tolerant.

9. A method for preparing a metal organic framework comprising:
    mixing a solid metal precursor with a solid ligand precursor to form a mixture of the solid precursors, wherein the solid metal precursor includes $M-SiF_6$, wherein M includes a metal;
    wetting the mixture of the solid precursors with one or more drops of water; and
    heating the wetted mixture at a first temperature and thereafter further heating the wetted mixture to a second temperature to obtain a three-dimensional metal organic framework structure.

10. The method of claim 9, wherein the metal of the solid metal precursor is selected from a group consisting of Ni, Cu, Zn, Fe, and Co.

11. The method of claim 9, wherein the metal includes Ni.

12. The method of claim 9, wherein the solid ligand precursor includes pyrazine, 4,4'-Bipyridin, 1,4-Diazabicyclo[2.2.2]octane, or 1,2-bis(4-pyridyl)acetylene.

13. The method of claim 9, wherein the solid ligand precursor includes a nitrogen-containing heterocyclic ligand.

14. A method for preparing a metal organic framework comprising:
    mixing a metal precursor with a ligand precursor to form a mixture, wherein the metal precursor includes $NiSiF_6$ and the ligand precursor includes pyrazine;
    adding water to the mixture;
    heating the mixture at a first temperature after the water is added to the mixture; and heating the mixture to a second temperature to obtain a three-dimensional metal organic framework structure.

15. The method of claim 9, further comprising forming SIFSIX-Ni-3 metal organic framework.

16. The method of claim 9, wherein the three-dimensional metal organic framework intermediate structure is $H_2S$ tolerant.

17. The method of claim 9, wherein the first temperature is less than the second temperature.

18. The method of claim 14, wherein the first temperature is less than the second temperature.

19. The method of claim 9, wherein the solid metal precursor includes one or more of $NiSiF_6$, $CuSiF_6$, $ZnSiF_6$, $CoSiF_6$, and $FeSiF_6$.

20. The method of claim 14, wherein the solid metal precursor includes one or more of $NiSiF_6$, $CuSiF_6$, $ZnSiF_6$, $CoSiF_6$, and $FeSiF_6$.

* * * * *